(12) United States Patent
Carlsson et al.

(10) Patent No.: US 6,208,813 B1
(45) Date of Patent: *Mar. 27, 2001

(54) METHOD AND ARRANGEMENT FOR TAKING PICTURES OF THE HUMAN BODY, ESPECIALLY OF THE MOUTH CAVITY

(75) Inventors: Lennart Carlsson, Molndal; Torsten Jemt, Lerum; Anders Lie, Bohus, all of (SE)

(73) Assignee: Nobelpharma AB, Goteborg (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/961,032

(22) Filed: Oct. 30, 1997

Related U.S. Application Data

(63) Continuation of application No. 08/495,621, filed as application No. PCT/SE94/01143 on Nov. 29, 1994, now abandoned.

(30) Foreign Application Priority Data

Dec. 6, 1993 (SE) .................................................... 9304041

(51) Int. Cl.$^7$ ................................................... G03B 35/00
(52) U.S. Cl. ........................................... 396/324; 396/331
(58) Field of Search ........................... 396/14, 16, 322, 396/324, 326, 327, 331, 333; 348/42, 45, 61, 66, 77; 352/57, 58, 60; 353/7; 359/462, 464

(56) References Cited

U.S. PATENT DOCUMENTS

| 4,009,951 | * | 3/1977 | Ihms ................................. 396/331 X |
| 4,096,502 | * | 6/1978 | Danko, Jr. et al. . |
| 4,123,768 | * | 10/1978 | Kilshaw et al. . |
| 4,837,732 | * | 6/1989 | Brandestini et al. . |
| 5,262,835 | | 11/1993 | Lindqvist et al. ................ 356/376 X |
| 5,320,462 | | 6/1994 | Johannsson et al. ............. 356/376 X |
| 5,372,502 | | 12/1994 | Massen et al. ......................... 433/215 |
| 5,424,836 | * | 6/1995 | Weise et al. ............................ 356/376 |

FOREIGN PATENT DOCUMENTS

| 186486 | 7/1907 | (DE) . |
| 880051 | 6/1953 | (DE) . |
| 0519915 B1 | 12/1992 | (EP) . |

OTHER PUBLICATIONS

The editors of Time–Life Books, *Photography As a Tool*, Time–Life Books, New York, pp. 204, 208, and 209, 1970.*

* cited by examiner

*Primary Examiner*—David M. Gray
(74) *Attorney, Agent, or Firm*—Connolly Bove Lodge & Hutz

(57) ABSTRACT

A camera and a method for taking stereophotographic pictures. The camera comprises a camera housing for carrying film, a film placement plate in the camera housing for positioning against a portion of the film to be exposed to ensure precise planar placement of the portion of film while exposed, a lens which is fixed to the camera housing to obtain optical and geometric stability, and at least one reflecting surface on the camera extending essentially parallel to and along a periphery of a linear imaging path from the lens and an object to be photographed, wherein the lens receives a first portion of the optical radiation which emanates directly from the object and produces an actual image of the object on the film and the at least one reflecting surface reflects a second portion of the optical radiation emanating from the object toward the lens and creates a virtual image of the object on the film, the virtual image having an viewing angle of the object different than the actual image.

5 Claims, 2 Drawing Sheets

METHOD AND ARRANGEMENT FOR TAKING PICTURES OF THE HUMAN BODY, ESPECIALLY OF THE MOUTH CAVITY

This application is a continuation of Ser. No. 08/495,621 filed on Aug. 3, 1995, now abandoned, which is a 371 of PCT/SE94/01143 filed Nov. 29, 1994.

TECHNICAL FIELD

The present invention relates to a method for taking pictures of the human body, especially of the mouth cavity, or of a model for artificial construction of a tooth, dentine, a pros thesis, etc., here called "objects", and for taking these pictures from at least two different angles. So-called stereophotography, that is photography for three-dimensional measurement, etc. may be appropriate in this respect. The method uses camera equipment which comprises a camera housing for film or other image-recording material, a lens system, which, when photographs are being taken, is aimed at one or more objects or object parts, for example an implant, tooth remnant, tooth, etc. Possible examples of image-recording material besides film (silver film) are digital video (CCD camera) or digital camera. The invention also relates to a camera for implementing the method.

BACKGROUND OF THE INVENTION

It is already known to use stereophotography in connection with producing dental articles and for dental work, in which case at least two cameras have generally been set up at a distance from one another and have been activated for taking pictures from different angles. It is also already known to use stereophotography in photogrammetric connections for measuring locations and positions of various surfaces, teeth, objects, etc. In order to be able to reach conclusions on the actual positions in space/the actual coordinate system, it is possible to use various aids, such as coordinate-measuring equipment, marked glass discs, etc.

There is a requirement facilitate the production of dental articles (dental bridges, e.g. dental caps, etc.) in a simpler way compared with present-day production methods. The invention is directed to solving this problem.

When producing dental bridges, prostheses and the like, a model is normally made at present by taking an impression with an impression compound in the mouth cavity. An object of the invention is to eliminate such modelling in the production of such dental articles.

The use of stereophotography is not entirely self-evident in this context, even if it does solve the problem of eliminating modelling with an impression compound. The use of two or more cameras for establishing stereophotographs presents problems, since it is difficult to prevent the patient from moving between two exposures. Even very small time delays between exposures and small movements of the patient, have a deleterious effect on the result. As a result, persons skilled in the art have heretofore concluded that the use of multiple cameras is not suited to everyday clinical use. The invention solves this problem and makes it possible for the present invention to be used in a practical application involving a patient.

Stereophotography must be able to provide a greater degree of accuracy or resolution in the dental product compared with previous uses of stereophotographic equipment. The invention solves this problem and also displays a greater degree of accuracy even in comparison with the use of the above mentioned modelling.

It has been shown that methods and arrangements used hitherto have led to static stress forces being built into the dental article/dental bridge in question. Even though these forces are relatively small, they lead in the long term to a collapse of all or part of the jaw bone in question. There is therefore a need for substantially greater accuracy of production than has previously been the case. The invention solves this problem too.

In connection with dental work in and around the mouth cavity, it is important that the photographic equipment employed have small dimensions and be easy to handle when in use. The space available in and around the patient's mouth cavity is limited, and the personnel providing the treatment should not need to possess any photographic expertise in order to perform their dental work. The invention solves this problem as well.

In accordance with the concept of the invention, the mirrors reflecting the optical radiation are used to form virtual lens functions which are arranged at a distance from one another to obtain a stereo imaging effect. In one embodiment, the interaction between the camera parts and the reflection surface(s) are locked in a mutual relationship at the site so that simplified use of the camera is achieved. The invention solves this problem too.

In a further embodiment, it is possible for the measurements in the images to be overdefined and for the positions of the lenses to be determined by means of solution of equation systems. This is also permitted by the invention.

There is a need to render more efficient all the operations surrounding the production of dental articles which are applied in the mouth cavity, with the whole production chain being taken into account, including examination of the patient's mouth and production in the actual material (titanium, for example) in the machine. The novel method and arrangement of the invention reveal new avenues for realizing such methods and arrangements and can be used, in connection with methods and the arrangements known in the art.

When working in the mouth cavity, it should be possible, for example, to effect imaging of a number of implants (2 to 6 implants, for example) in a jaw bone both at the level of the fixture and at the level of the spacer. The invention solves this problem.

SUMMARY THE INVENTION

The feature which can principally be regarded as characterizing a method according to the invention is that optical radiation emanating from a respective object or object part is reflected on one or more radiation-reflecting reflection surfaces, which are situated between the respective object or object part and the lens system, before passing through the lens system to the film in the camera housing to obtain at least two lens functions which are situated at a distance from one another and of which at least one is virtual. Two or more different images of the respective object or object part are generated with the lens functions from the different angles at one and the same exposure.

In a preferred embodiment, the optical radiation from the respective object or object part is made to pass an end surface on a unit which is provided with one or more inner walls, each forming a reflection surface.

The feature which can principally be regarded as characterizing a camera according to the invention is that it is arranged with one or more reflection surfaces situated between the lens system and the respective. object/object part or tooth/tooth replacement, and that the reflection surface(s) reflect optical radiation emanating from the respective object or tooth/tooth replacement, or part thereof, before the optical radiation passes through the lens system and reaches the film or equivalent. Further characteristics are that the one or more reflection surfaces arranged to establish at least two lens functions which are situated at a distance from one another, of which at least one lens function is virtual. The lens functions produce, on film, images from different angles at one and the same exposure.

In a further embodiment, the reflection surfaces are two in number, and the reflection surfaces extend essentially parallel to the viewing direction of the camera. In this way, three images of the respective object or tooth/tooth replacement, or part thereof, are obtained on the film during the same exposure. This is achieved because the two virtual lens functions occur together with the lens function performed by the lens system.

In one embodiment, the camera comprises a standard camera provided with a flash function, for example a 35-mm miniature camera with, for example, a 24-mm wide-angle lens. This basic construction is known per se and is a in this case, provided with the reflection surface(s) or mirror surface(s). The real or actual lens is preferably arranged in a fixed manner on the camera housing, for example by means of glue, to obtain optical and geometric stability. Members, for example a glass disc, can be arranged to ensure that the film is applied with great evenness/precision to a plane surface. Thus, the film should not deviate from the plane by more than ±0.1 mm, for example.

In a further embodiment, each reflection surface is situated on a prism body which is mounted on the camera opening. The body in this case supports the reflection surface or the reflection surfaces on one or more inner walls. The optical radiation passes, via the body, through an end surface which is directed towards the respective object/object part or tooth/tooth replacement part. In one embodiment, the arrangement with the camera and the reflection surface(s) or mirror(s) are designed to image areas of the order of magnitude of 50×100 mm. The arrangement operates at a distance from the respective object/object part or tooth/tooth replacement (part) which is of the order in magnitude of 50–100 mm. The imaging on the film can take place at a scale of 1:4.

The arrangement is also characterized in that the error in the imaging of the respective object/object part or tooth/tooth replacement part is of the order of magnitude of 0.02 mm for distinct points. The camera can be calibrated in its entirety with an accuracy which lies in the region of 0.005 mm on the image scale.

ADVANTAGES

By means of what has been proposed above, a conventional miniature camera with flash unit can form the basis for the structure or the basic construction. The camera is handled in the normal way and, by virtue of its small format, is easy to manage and easy to use close to the patient's mouth. The patient experiences less discomfort during identification of, for example, positions and inclinations on implants in one or both jaws. Accurate calibration can be performed, and the costs of the camera can be kept relatively low. The camera equipment can be employed in novel methods and arrangements for the production of artificial support members. An annular flash unit can be mounted between the lens and the reflecting surface/mirror.

DESCRIPTION OF THE FIGURES

A presently proposed embodiment of a method and arrangement according to the invention will be described hereinbelow with reference to the attached drawings, in which.

DETAILED DESCRIPTION OF PREFERRED EMBODIMENTS

Figure 1:
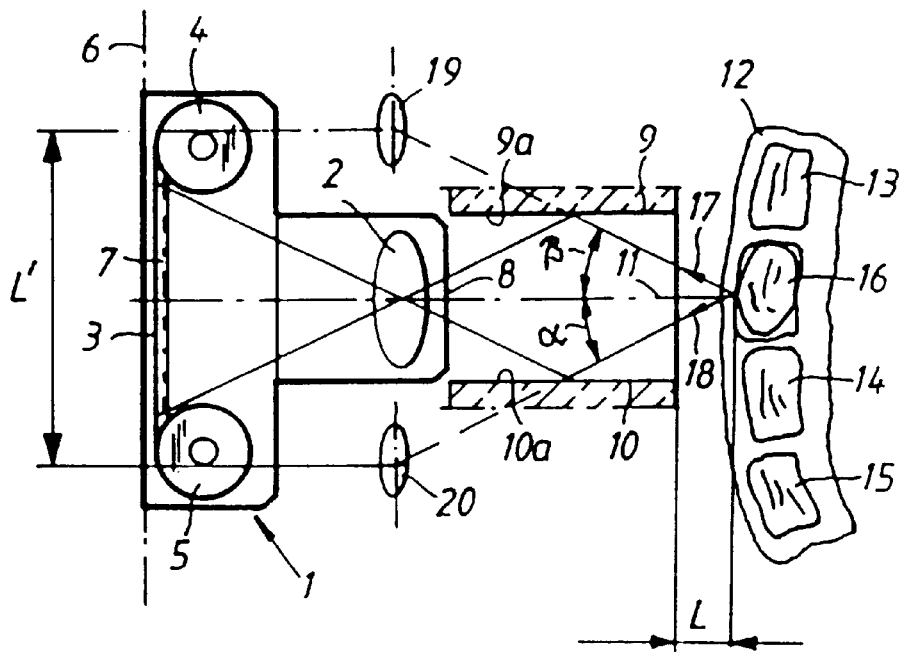
FIG. 1 shows, in a top view, the camera in relation to the lower jaw of a patient.

In FIG. 1, a camera housing is indicated by 1. Arranged in the camera housing is a lens system comprising a lens 2 known type. Also included in the camera housing is an arrangement for a film 3 which is disposed and can be advanced on film spools 4 and 5. The film is acted on so as to be placed with great precision in plane 6 at the back of the camera. The action is effected by means of a glass plate 7 positioned against the film so that the latter assumes its position in the plane 6 with the precision mentioned above. Arranged at the opening 8 of the camera housing are first and second reflecting surfaces or mirrors which extend perpendicularly to the plane of the figure. The mirrors extend parallel to the longitudinal axis 11 of the camera or the main direction of the camera. The mirroring or reflecting surfaces 9 and 10 can themselves have other orientations, although the parallel orientation shown is preferably used. The camera is aimed at the mouth cavity of a patient as represented by a jaw bone 12 the jaw bone there are teeth 13, 14, 15, an implant 16, dental bridge, etc. The radiation emanating from the imaged area in the mouth cavity is indicated by the lines 17, 18. This optical radiation is reflected on the inner surfaces 9a and 10a of the mirrors before it passes through the lens 2 and reaches the film 3. The arrangement means that two virtual lens functions 19, 20 arise, which in turn means that three image fields appear on the film 3. The first image field is caused by the real lens 2, and the second and third image fields are caused by the virtual lens functions 19 and 20. Three images are thus obtained on the picture and can be compared, for example in computer equipment for determining surfaces of the teeth, the implants, etc. The lens functions are arranged essentially parallel. In this connection, reference is made to the Swedish patent application [lacuna], which has the same filing date as the present Swedish patent application.

The camera is of standard design and is of the type which has been specified above. The miniature camera can be placed at a distance L of about 50–100 mm from the patient's mouth.

Figure 2:
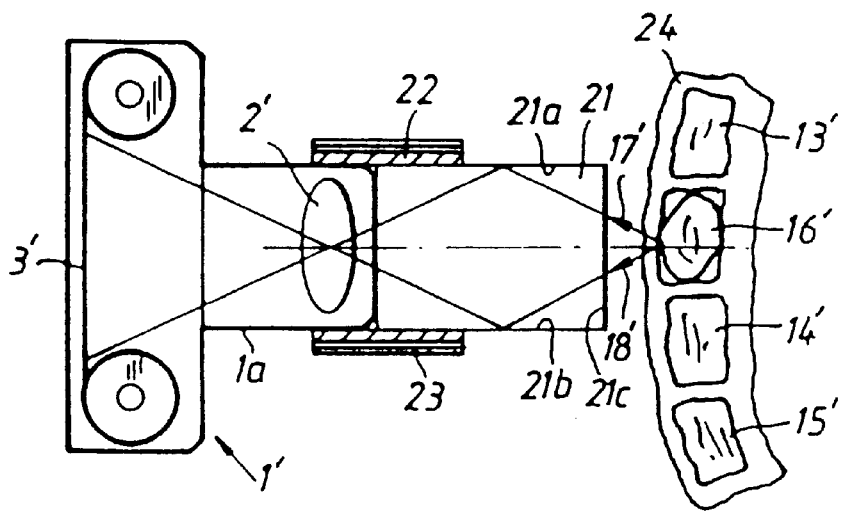
FIG. 2 shows, in a top view, the camera in relation to objects or object parts on a model.

FIG. 2 shows the camera 1' with the same basic construction as in FIG. 1. In this case, a prism 21 is used which has two parallel inner walls 21a and 21b which correspond to the reflecting surfaces 9a and 10a indicated in FIG. 1. The prism is secured to the camera housing 1a. The same applies to the lens 2', which is secured to the camera housing by means of glue or the equivalent. The securing of the prism 21 to the camera housing 1a is symbolized by a tubular part 22. The camera is provided with an annular flash 23 of a type known per se. The flash arrangement is arranged concentrically on the said sleeve-shaped member 22. The radiation 17', 18' enters the free end surface 21c of the prism 21 and is reflected onto the inner surface 21a, 21b before it passes through the lens 2' and reaches the film 3'. The imaging can in this case be carried out on a patient, a model 24, etc.

Figure 3:
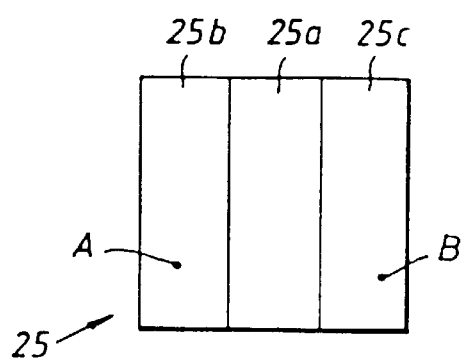
FIG. 3 shows a photograph taken with the camera according to FIGS. 1 and 2, in which photograph there are two images of two given discrete points.

FIG. 3 shows a photograph 25 comprising three sections 25a, 25b and 25c. The section 25a corresponds to the image, of the actual object or body part, which is effected by the lens 2'. Sections 25b and 25c correspond to the image areas which are generated by the virtual lenses 19 and 20. The virtual lenses are separated by a distance L' (see FIG. 1). The images in the image fields 25b and 25c thus represent the body part or the object seen from two different angles, alpha and beta respectively (see FIG. 1). A corresponding point is present in the image field 25a, which point does not, however, need to be used (even though it is possible to do so) in the present case for determining the positions of the relevant objects, surfaces or points thereon.

Figure 4:
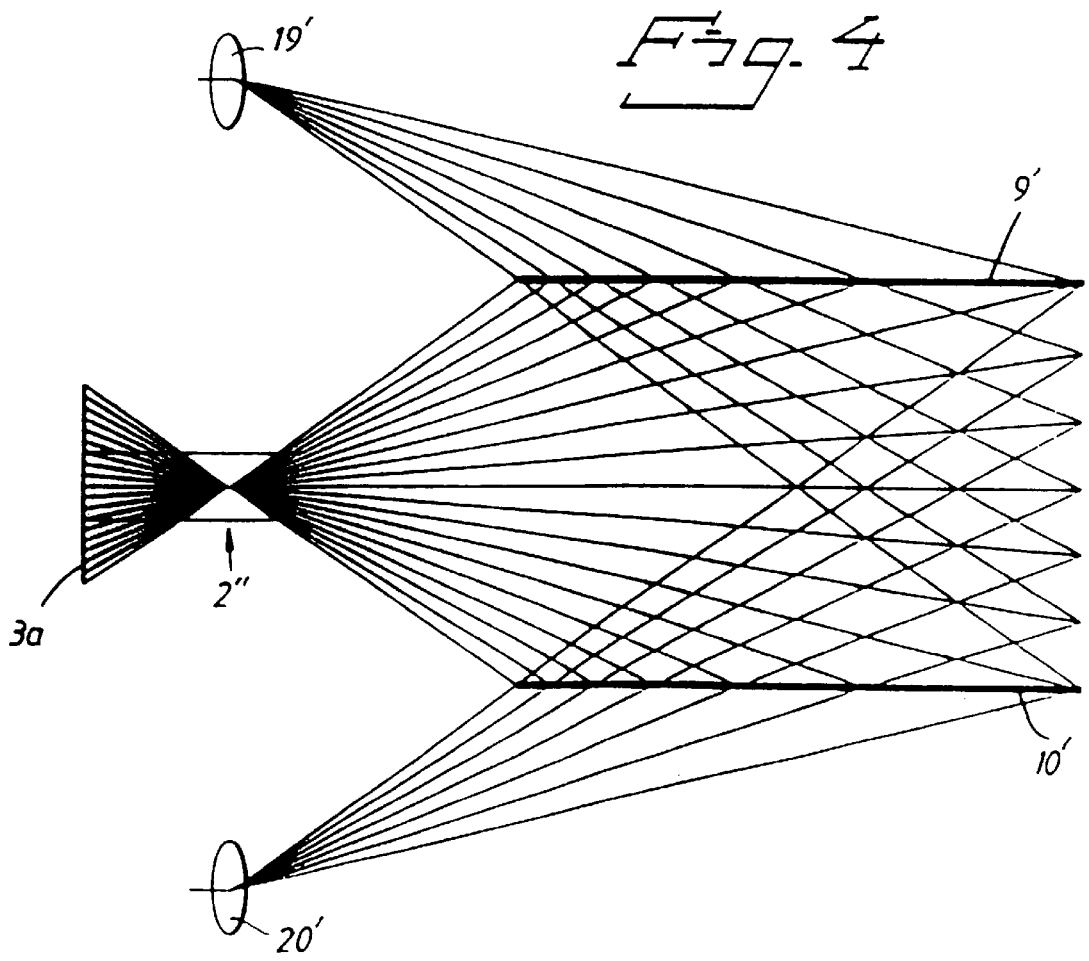
FIG. 4 shows, in longitudinal section, the optical ray path in the camera where reflecting surfaces are used to obtain virtual lens functions arranged at a distance from one another for achieving the stereo imaging effect.

FIG. 4 shows the relevant part of the optical ray path in the novel camera. The reflecting surfaces or the mirrors are shown by 9' and 10', and the virtual lens functions are shown by 19', 20'. The real or actual lens is indicated by 2" and the film plane by 3a.

The invention is not limited to the embodiment shown hereinabove by way of example, but instead can be modified within the scope of the attached patent claims and the inventive concept.

What is claimed is:

1. A method for taking stereophotographic pictures of image areas in a mouth cavity of a human being comprising:

providing a miniature camera housing having a film placement plate arranged in said camera housing between film and a lens for positioning against a portion of film to be exposed to ensure precise planar placement of said portion of film while exposed, said camera adapted to take pictures of said image areas on the order of magnitude of 50×100 mm;

securing said lens to said camera housing to obtain optical and geometric stability;

placing said camera about 50–100 mm outside said mouth cavity:

aiming said lens at an object to be photographed in said mouth cavity so as to receive a first portion of optical radiation emanating directly from said object to be photographed and produce an actual image of said object on said film; and attaching at least one reflecting surface to said camera housing essentially parallel to a linear imaging path from the lens to said object to be photographed so as to reflect a second portion of said optical radiation emanating from said object toward said lens creating a virtual image of said object on said film, said virtual image having a viewing angle of the object different than the actual image to obtain an imaging error of +/−0.02 mm for distinct points on the object and a calibration accuracy of approximately 0.005 mm.

2. The method for taking stereophotographic pictures according to claim 1 further comprising the steps of providing a prism having said at least one reflection surface on inner walls; and mounting said prism between said lens and said object to be photographed wherein a front face of said prism is adjacent said lens, and a back face of said prism receives optical radiation from said object to be photographed; wherein said lens receives said first portion of said optical radiation emanating directly from said object through said prism and produces said actual image of said object on said film; and said at least one reflection surface of said prism reflects said second portion of said optical radiation emanating from said object toward said lens, creating said virtual image of said object on said film, said virtual image having an viewing angle of the object different than the actual image.

3. A camera for taking stereophotographic pictures according to claim 1 further comprising the step of placing said at least one reflection surface in a reflection plane.

4. A miniature camera for taking stereophotographic pictures of image areas in a mouth cavity of a human being comprising:

a camera housing for carrying film;

a film placement plate, arranged in said camera housing between said film and a lens, for positioning against a portion of said film to be exposed to ensure precise planar placement of said portion of film while exposed;

said lens being fixed to said camera housing to obtain optical and geometric stability; and at least one reflecting surface extending essentially parallel to a linear imaging path from the lens to an object to be photographed;

said lens receiving a first portion of optical radiation emanating directly from said object and producing an actual image of said object on said film;

said at least one reflecting surface reflecting a second portion of said optical radiation emanating from said object toward said lens creating a virtual image of said object on said film, said virtual image having a viewing angle of the object different than the actual image;

wherein said camera has an imaging error of +/−0.02 mm for distinct points on the object and a calibration accuracy of approximately 0.005 mm and wherein said camera is adapted to take pictures of said image areas on the order of magnitude of 50×100 mm and to operate at a distance of about 50–100 mm from said mouth cavity.

5. A camera for taking stereophotographic pictures according to claim 4 further comprising.

a prism fixedly mounted via a tubular member surrounding a part of said prism and said lens to said camera to obtain optical and geometric stability, said prism being located between said lens and an object to be photographed, said prism comprising said at least one reflecting surface on inner walls of said prism, a front face adjacent said lens, and a back face for receiving optical radiation into said prism from said object to be photographed;

a flash unit arranged concentrically on said tubular member; wherein said lens receives said first portion of said optical radiation emanating directly from said object through said prism and produces an actual image of said object on said film; and said at least one reflecting surface of said prism reflects said second portion of said optical radiation emanating from said object toward said lens, creating a virtual image of said object on said film, said virtual image having an viewing angle of the object different than the actual image.

* * * * *